United States Patent [19]

Urban et al.

[11] 4,409,843

[45] Oct. 18, 1983

[54] DEVICE FOR MEASURING TABLET BREAKING FORCE

[75] Inventors: Joseph J. Urban, Richboro, Pa.; Norman L. Henderson, Gladstone, N.J.

[73] Assignee: Hoechst-Roussel Pharmaceuticals Inc., Somerville, N.J.

[21] Appl. No.: 357,109

[22] Filed: Mar. 11, 1982

[51] Int. Cl.³ .......................... G01N 3/20; B26F 3/00
[52] U.S. Cl. ...................................... 73/851; 30/124; 225/103
[58] Field of Search .......................................... 73/851

[56] References Cited

U.S. PATENT DOCUMENTS

| | | | |
|---|---|---|---|
| 2,041,869 | 5/1936 | Smith et al. | 265/18 |
| 2,627,640 | 2/1953 | Garnich | 25/1 |
| 3,371,833 | 5/1968 | Sutton | 225/2 |
| 3,507,426 | 4/1970 | Bielen et al. | 225/2 |
| 3,650,445 | 3/1972 | Heltzman | 225/93 |
| 3,815,802 | 6/1974 | Stevens | 225/93 |
| 4,159,568 | 7/1979 | Berner | 30/124 |
| 4,173,826 | 11/1979 | Leopoldi et al. | 30/124 |
| 4,179,806 | 12/1979 | Lieptz | 30/124 |
| 4,199,863 | 4/1980 | Deckert | 30/124 |
| 4,226,376 | 10/1980 | Pfleger | 241/99 |

FOREIGN PATENT DOCUMENTS 2086715 12/1971 France .

OTHER PUBLICATIONS

Shotton et al., "The Strength of Compressed Tablets", J. Pharm. Sci., 12, (1960), pp. 87T–92T.
Shotton et al., "The Strength of Compressed Tablets—Part II", J. Pharm. Sci., 12 (1960) pp. 93T–96T.
Fairchild et al., "Pfizer Tablet Hardness Test", J. Pharm. Sci., 50, 11 (1961) pp. 966–969.
Endicott et al., "New Instrument and Method for Evaluating Tablet Fracture Resist.", J. Pharm. Sci., 50, 4 (1961) pp. 343–346.
Brook et al., "Crushing-Strength of Compressed Tablets I", J. Pharm. Sci., 57, 3 (1968) pp. 481–484.

Primary Examiner—Howard A. Birmiel

[57] ABSTRACT

There is provided a device for measuring the force required to break a tablet, wherein the device comprises a tablet holding means comprising a base, a tablet splitting edge in the base and an area for holding a tablet in an inclined cantilevered position such that at least a portion of the cantilevered segment of the tablet extends over the tablet splitting edge. Means are provided for exerting a force substantially normal to a portion of the cantilevered segment of the tablet extending over the splitting edge to thereby create a moment of force about the tablet splitting edge sufficient to break the tablet. The device includes means for measuring the force required to break the tablet.

6 Claims, 5 Drawing Figures

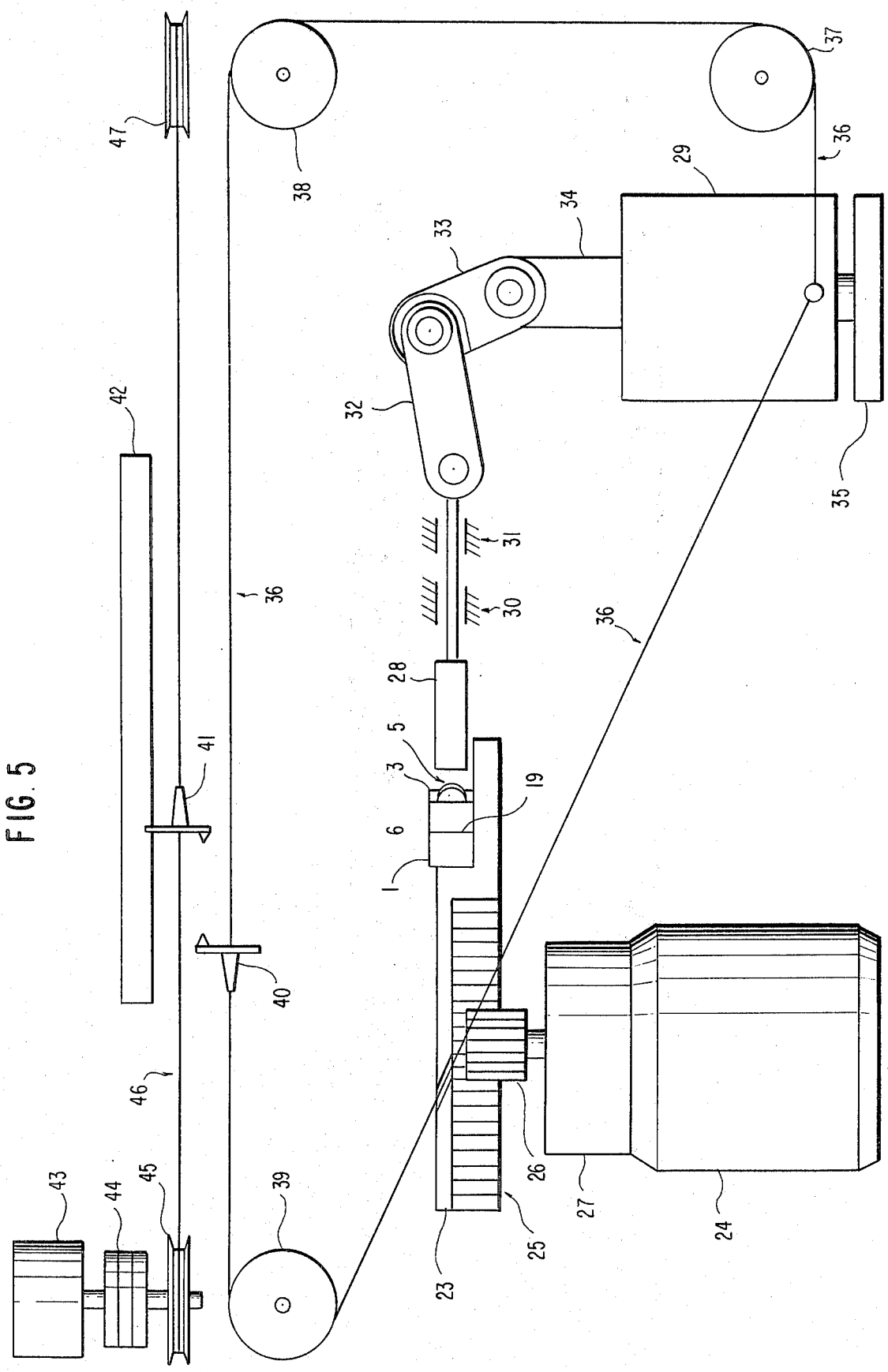

DEVICE FOR MEASURING TABLET BREAKING FORCE

BACKGROUND OF THE INVENTION

This invention relates to a device for breaking a tablet, and in particular to a device for measuring the force required to break the tablet.

Tablets have long been convenient dosage forms for a variety of materials, such as medicaments, vitamins, foods and detergents. It is important that each tablet be of the same weight and content of active material within close limits in order to ensure a constant dosage. In addition, each tablet must have sufficient hardness to withstand the shock of handling, packing and shipping. This latter requirement led to the development of hardness testers, such as the Strong-Cobb, Stokes-Monsanto, Pfizer and Heberlein hardness testers. These well-known devices are based on the same principle of operation, namely, diametral crushing of a tablet.

In the Strong-Cobb tester, the force required to break a tablet across the diameter is produced by a manually or pressure operated pump. As the pressure increases, a plunger is forced against a tablet set on edge. A dial indicator records the final breaking force.

The Pfizer hardness tester operates on the same mechanical principle as ordinary pliers. As the tablet is crushed in the jaws of the device, the force is recorded on a dial indicator. The dial indicator remains at the reading where the tablet breaks. It returns to zero when a reset button is pressed.

The Stokes-Monsanto tester consists of a barrel containing a compressible spring held between two plungers. The lower plunger is brought into contact with the tablet. The upper plunger is forced against the spring by a threaded bolt and the force is transmitted against the tablet. As the spring is compressed, a pointer rides along a gauge in the barrel and indicates the pressure at which the tablet fractures.

The Heberlein tester operates in a horizontal position. A moving anvil presses the tablet against a stationary anvil. As force is applied to the edge of the tablet, a pendulum swings away from its normal position. Its movement is followed by a pointer moving along a scale indicator. When the tablet breaks, the pendulum swings back to its original position while the pointer indicates the scale reading in both kilograms and in Strong-Cobb units.

Compressed tablets are frequently orally administered to animals and humans. While tablets for animal and human consumption are normally available in unit dosages, it is frequently necessary to reduce the dose, such as by breaking the tablet in half, and consuming only half the tablet. Traditionally, tablets have been broken by hand. This can be accomplished by breaking the tablet between the second and third fingers of one hand while the thumb is used as a fulcrum or by using the index fingers of both hands while the thumbs serve as a fulcrum.

It is important for the tablet formulator to have some indication of the force that will be required to break the tablet by hand. Tablets can then be formulated for specific uses. For example, persons with decreased strength in the hands or those suffering from diseases, such as arthritis, or those with handicaps, such as amputees, may encounter considerable difficulty in breaking tablets. The tablet formulator can provide such individuals with tablets that require a relatively low breaking force.

When the tablets are manufactured, the manufacturer must be able to determine the breaking strength of the tablets for quality control purposes.

Thus, there exists a need in the art for a tablet breaking device capable of measuring the force required to break the tablet. The measured force should be representative of the force that will be required for a human to break a similar tablet using one of the traditional manual methods. The tablets should break evenly in the device without crushing. Ideally, the device should be of relatively simple construction, easy to manufacture and simple to operate.

SUMMARY OF THE INVENTION

Accordingly, this invention aids in fulfilling these needs in the art. Specifically, this invention provides a device for measuring the force required to break a tablet, wherein the device comprises a tablet holding means comprising a base, a tablet splitting edge in the base and an area for holding a tablet in an inclined cantilevered position such that at least a portion of the cantilevered segment of the tablet extends over the tablet splitting edge. Means are provided for exerting a force substantially normal to a portion of the cantilevered segment of the tablet extending over the splitting edge to thereby create a moment of force about the tablet splitting edge sufficient to break the tablet. The device includes means for measuring the force required to break the tablet.

The device of this invention thus not only measures the force required to break a tablet, but also gives a measure that is representative of the force required for a human to break a similar tablet. As will be apparent from the description that follows, the device of the invention is simple to operate and can be adapted for use with a variety of different size tablets.

BRIEF DESCRIPTION OF THE DRAWINGS

This invention will be more fully understood by reference to the following drawings, in which like numerals identify like parts:

FIG. 5 is a schematic diagram of a tablet breaking device of the invention embodying the tablet holding means of FIG. 3.

DETAILED DESCRIPTION

Figure 1:
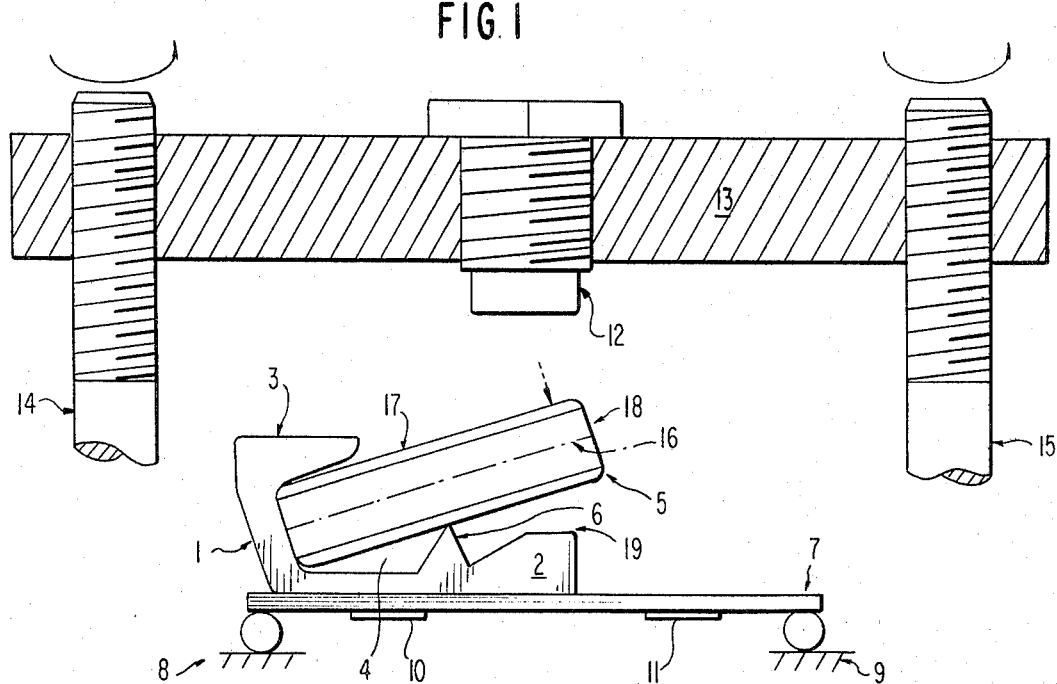
FIG. 1 is a schematic diagram of a tablet breaking device of the invention.

Referring to FIG. 1, it will be seen that the device comprises a tablet holding means 1 comprising base 2 having a top surface 3 and an area 4 for supporting a bolus tablet 5 such that a portion of the tablet extends beyond the top surface 3. More particularly, the tablet 5 is held in an inclined, cantilevered position with at least a portion of the cantilevered segment of the tablet extending over a tablet splitting edge 6. The tablet splitting edge 6 is contiguous with the tablet holding area 4 and these elements are unitary with the base 2 of the tablet holding means 1.

Tablet holding means 1 is positioned on a substantially flat plate 7 on support members 8 and 9. Underneath plate 7 are strain gauges 10 and 11, which are connected to an indicating device (not shown).

Provided above the tablet holding means 1 are means for exerting a force substantially normal to the portion of the cantilevered segment of the tablet 5 extending over the splitting edge 6. The means for exerting the force comprises a platen 12 rigidly secured to a substantially horizontal arm 13, which can be driven upwardly and downwardly over the threads of screws 14 and 15. The screws 14 and 15 can be rotated at constant rate. As the platen 12 approaches tablet 5 in the tablet holding means 1, the platen will eventually contact the tablet. The force applied to tablet 5 via platen 12 has a component F substantially perpendicular to the diameter 16 of the tablet 5. As depicted in FIG. 1, surface 17 of tablet 5 is parallel to the diameter 16. Continued application of force on the tablet 5 will result in a statically determinant system, and if sufficient force is applied, the tablet 5 will break.

When the force F is applied to tablet 5, a moment of force is thereby created about the splitting edge 6, and this moment of force is sufficient to break the tablet 5 into two pieces, one piece being that in the tablet holding area 4 and the other piece corresponding to the portion extending over the tablet splitting edge 6. As depicted in FIG. 1, the tablet splitting edge 6 is below the tablet 5, and when the tablet is broken, the broken portion (corresponding to the cantilevered segment) will rest on surface 19 of tablet holding means 1 and will be below the top surface 3.

Force F in FIG. 1 applied to surface 17 of tablet 5 proximate the outer edge 18 of the tablet is the only force that needs to be applied to cleanly break the tablet. For this reason, the force F can be termed the "breaking force". It is not necessary to apply forces along the remaining portions of the surface 17; such forces would tend to form compressive stresses and cause the tablet to crumble. The breaking force is alone sufficient to cause the tablet to snap.

The breaking force can be determined by any suitable load measuring device. The measurement of loads by mechanical, electrical and optical principles is well known. An electrical resistance strain gauge, such as a metallic wire or semiconductor, is shown in FIG. 1. The strain gauges can be connected to a Wheatstone bridge circuit coupled to a meter via a suitable amplifier circuit. Such devices are commercially available. By calibrating the device against known standards, the breaking force can be simply measured.

Figure 2:
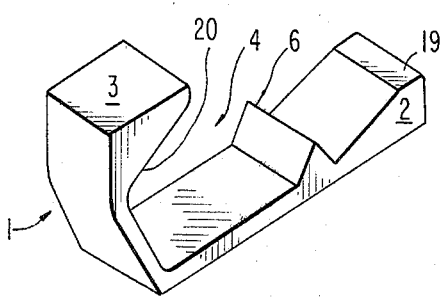
FIG. 2 is a perspective view of the tablet holding means of FIG. 1.

The tablet holding means 1 of FIG. 1 is shown in greater detail in FIG. 2. It will be seen that the tablet holding means 1 comprises base 2, tablet splitting edge 6 and area 4 for holding the tablet in position. A rigid tablet restraining arm 20 unitary with the base 2 prevents upward movement of the tablet when the breaking force is exerted proximate the outer edge 18 (FIG. 1) of the tablet. The breaking force is balanced by a force exerted on the other extremity of the tablet by the tablet restraining arm 20. Thus, forces can be exerted only at the extremities of the tablet to obtain the maximum moment of force about the splitting edge. The tablet splitting edge 6 forms a protrusion in the tablet holding area 4. Preferably, the tablet splitting edge 6 has a width substantially corresponding to the width of the tablet where the tablet is to be broken.

Figure 3:
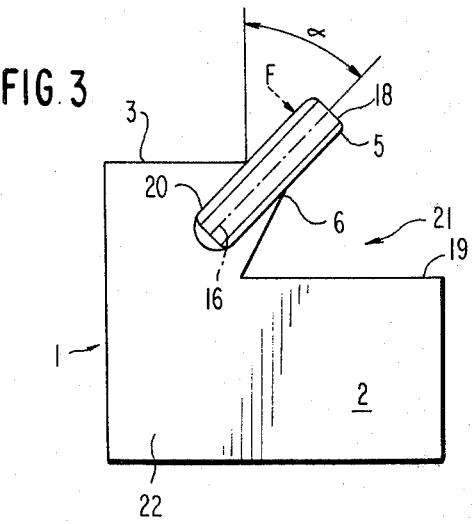
FIG. 3 is a view of another tablet holding means for use in the invention.
Figure 4:
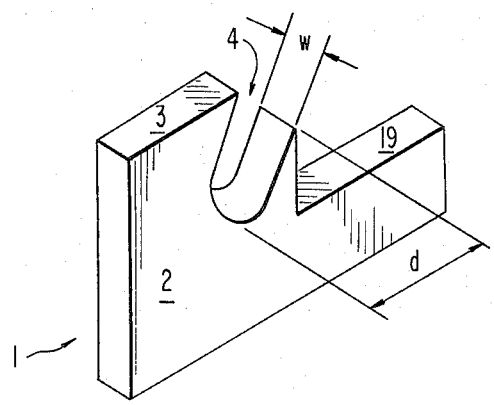
FIG. 4 is a perspective view of the tablet holding means of FIG. 3.

The construction of another tablet holding means for use in the invention is shown in detail in FIGS. 3 and 4. Referring to these Figures, the tablet holding means 1 has a base 2, a top surface 3 and an area 4 for holding the tablet. The holding area 4 comprises an elongated opening or slot of substantially constant cross-sectional area throughout its width in the top surface 3 of the base 2. The area 4 extends from side to side of base 2. The tablet holding means 1 includes an area 21, which defines a cavity for receiving the broken portion of tablet 5.

It will be appreciated that the tablet holding means can be adapted to accommodate tablets of different dimensions. For instance, the tablet holding means 1 can be made to accommodate tablets of different size by altering the depth (d) or the width (w) or both the depth and the width of tablet holding area 4 (see FIG. 4). The tablet holding means of FIg. 3 is preferred for use with small tablets, such as tablets having a length or diameter of about 50 to about 200 mm. The tablet holding means of FIG. 2 is suitable for use with larger tablets, such as tablets having a length or diameter of about 200 to about 700 mm. The device of this invention can be used with tablets having a round, oblong, capsule or similar shape.

Another device of the invention for measuring tablet breaking force is shown in FIG. 5. The device depicted is a modified Schleuniger (Switzerland) tablet hardness tester. The device comprises a powerized jaw 23 driven by a motor 24 via rack 25, pinion 26 and transmission 27.

As depicted in FIG. 5, a tablet 5 is positioned in a tablet holding means 1 on powerized jaw 23. Tablet holding means 1 in FIG. 5 is the same as the tablet holding means 1 shown in FIGS. 3 and 4. In FIG. 5, the tablet holding means of FIG. 3 is positioned on its side opposite side 22 in FIG. 3, with the tablet in the position shown.

Opposite the tablet 5 is a measuring jaw 28 connected to a counterweight 29 via thrust bearings 30 and 31 and linkages 32, 33, 34. A calibration weight 35 is provided for calibrating the device.

The powerized jaw 23 driven by the motor 24 presses the tablet 5 against the measuring jaw 28 connected to the counterweight 29. A wire cord 36 is attached to counterweight 29 and travels over pulleys 37, 38 and 39. Attached to the wire cord 36 is a drag contact 40, which moves as the wire cord 36 moves. As drag contact 40 moves to the right, it contacts a pointer 41, which shows the force applied to the tablet 5 on a linear scale 42.

When the tablet 5 breaks, the contact between drag contact 40 and pointer 41 is interrupted. The motor 24 returns the powerized jaw 23 to its initial position. The pointer 41 remains adjacent the scale 42 to indicate the breaking force. At the start of the next test, the pointer 41 is first returned to its zero position by reset motor 43 via an electromagnetic clutch 44, which drives pulley 45. Another wire cord 46 is threaded over pulley 45 and pulley 47. Pointer 41 is secured to wire cord 46.

The devices depicted in FIGS. 1 and 5 can accommodate a variety of tablets of different size. The only modification that needs to be made is modification of the tablet holding means to accommodate the size of the tablet. As previously noted, this can be readily accomplished by altering the dimensions of the tablet holding area 4 and interchanging different tablet holding means in the device.

The significance of the broken tablet receiving area 21 (FIG. 3) will also be appreciated from the device shown in FIG. 5. When the tablet 5 is broken, the broken portion corresponding to the cantilevered segment falls into the area 21 free of the measuring jaw 28. The broken portions of the tablet do not interfere with further movement of machine elements or operation of the machine and can be readily removed when the machine cycle is completed.

As depicted in the Figures, the tablet splitting edge 6 is a straight, stationary edge formed from part of the base 2 of the tablet holding means 1. It is to be understood that the tablet splitting edge could also be a knife or blade installed in the base 2, but this embodiment is less preferred because additional assembly is reqired. Also, the tablet splitting edge could be serrated or located at a variety of distances from the top surface 3, provided that the tablet was adequately supported.

The tablet is held in the tablet holding means in an inclined, cantilevered position with at least a portion of the cantilevered segment of the tablet extending over the tablet splitting edge. In the tablet holding means shown in FIG. 3, the outer edge 18 of tablet 5 is perpendicular to the diameter 16 of the tablet, which makes an angle ($\alpha$) with the vertical equal to about 45°. The corresponding angle for the tablet shown in the tablet holding means 1 in FIG. 1 is about 70°. Typically, the angle ($\alpha$) will be in the range of about 10° to about 85°. Preferably, this angle will be about 45° to about 75°. For small tablets the angle ($\alpha$) will typically be about 45° to about 85° and for larger tablets about 10° up to about 45°.

It is not necessary that the entire portion of the tablet to be broken extend beyond the top surface 3 of the tablet holding means 1. In fact, it is not necessary that any portion of the cantilevered segment of the tablet extend beyond the top surface, provided that the tablet breaking means, such as measuring jaw 28 in FIG. 5, is sufficiently offset so that the top surface does not obstruct movement of the tablet breaking means.

The tablet breaking device of this invention makes it possible to evenly break tablets without crushing the tablet or causing the tablet to crumble. In addition, the breaking force measured is representative of the force required for a human to break a similar tablet. The device of this invention can be adapted to breaking tablets having a variety of sizes.

What is claimed is:

1. A device for measuring the force required to break a tablet, wherein the device comprises:
    (a) tablet holding means comprising a base, a tablet splitting edge in the base and an area for holding a tablet in an inclined cantilevered position such that at least a portion of the cantilevered segment of the tablet extends over the tablet splitting edge;
    (b) means for exerting a force substantially perpendicular to a portion of the cantilevered segment of the tablet extending over the splitting edge to thereby create a moment of force about the tablet splitting edge sufficient to break the tablet; and
    (c) means for measuring the force required to break the tablet.

2. Device according to claim 1 wherein the base includes cavity means for receiving a broken portion of the tablet.

3. Device according to claims 1 or 2 in which the base has a top surface provided with an opening for holding the tablet at an angle of about 45° to about 85° relative to the vertical.

4. Device according to claims 1 or 2 in which the base has a top surface provided with an opening for holding the tablet at an angle of about 10° up to about 45° relative to the vertical.

5. Device according to claim 1 wherein a breaking force is applied to the tablet proximate the outermost edge of the cantilevered segment of the tablet.

6. Device according to claim 1 wherein the tablet holding means comprises a tablet holding area and a rigid tablet restraining means over the tablet holding area for substantially preventing movement of the tablet when a breaking force is exerted thereon.

* * * * *